(12) United States Patent
Cullen et al.

(10) Patent No.: US 8,491,852 B2
(45) Date of Patent: Jul. 23, 2013

(54) MARKER OF WOUND INFECTION

(75) Inventors: Breda Mary Cullen, Skipton (GB); Rachael Clark, Skipton (GB); Philip Stephens, Cardiff (GB); Ryan Moseley, Mid-Glamorgan (GB)

(73) Assignee: Systagenix Wound Management (US), Inc. (GB)

( * ) Notice: Subject to any disclaimer, the term of this patent is extended or adjusted under 35 U.S.C. 154(b) by 715 days.

(21) Appl. No.: 11/914,884

(22) PCT Filed: Apr. 24, 2006

(86) PCT No.: PCT/GB2006/001467
§ 371 (c)(1),
(2), (4) Date: Aug. 25, 2008

(87) PCT Pub. No.: WO2006/123091
PCT Pub. Date: Nov. 23, 2006

(65) Prior Publication Data
US 2009/0299161 A1 Dec. 3, 2009

(30) Foreign Application Priority Data
May 20, 2005 (GB) .................................. 0510340.3

(51) Int. Cl.
*G01N 33/52* (2006.01)
(52) U.S. Cl.
USPC ............. 422/430; 422/420; 422/408; 436/62; 436/63; 436/69; 436/810

(58) Field of Classification Search
USPC ................ 422/55, 56, 58, 99, 104, 430, 420, 422/408; 436/62, 63, 69, 810
See application file for complete search history.

(56) References Cited

U.S. PATENT DOCUMENTS

| 5,789,255 | A | 8/1998 | Yu | |
|---|---|---|---|---|
| 6,375,896 | B1 * | 4/2002 | Wuske et al. | 422/411 |
| 7,601,546 | B2 * | 10/2009 | Bayloff et al. | 436/514 |
| 2003/0134332 | A1 * | 7/2003 | Boykin, Jr. | 435/7.1 |
| 2006/0127461 | A1 * | 6/2006 | Bloor | 424/445 |

FOREIGN PATENT DOCUMENTS

| GB | 2402880 | | 12/2004 |
|---|---|---|---|
| GB | 2408207 | * | 5/2005 |
| JP | 10-287872 | | 10/1998 |
| WO | 00/08203 | | 2/2000 |
| WO | 03/063693 | | 8/2003 |
| WO | 2010/133589 | | 11/2010 |

* cited by examiner

*Primary Examiner* — Monique Cole
(74) *Attorney, Agent, or Firm* — Stephen B. Salai, Esq.; Paul A. Leipold, Esq.; Harter Secrest & Emery LLP (57) ABSTRACT

An indicator device adapted give a detectable signal when the antioxidant capacity of a sample of a mammalian wound fluid exceeds a predetermined minimum level which is characteristic of an infected wound. Also provided system for use in the diagnosis and treatment of wounds comprising the inventive diagnostic device and a wound dressing comprising at least one antimicrobial agent for selective application to infected wounds. Also provided are methods of diagnosis and treatment by means of the inventive device and system.

14 Claims, 3 Drawing Sheets

MARKER OF WOUND INFECTION

CROSS REFERENCE TO RELATED APPLICATION

This application is the national stage of Application No. PCT/GB2006/001467, filed 24 Apr. 2006, which application claims priority from GB 0510340.3, filed 20 May 2005, which are all incorporated by reference herein in their entireties.

TECHNICAL FIELD

This invention relates to methods for the early detection and/or quantification of wound infection and to devices and wound dressings for use in connection with such methods.

BACKGROUND ART

The development of wound infection is a problem for many patients. Infected wounds can cause distress from associated morbidity and mortality, increased length of hospital admission, delayed wound healing and increased discomfort. Early recognition of the signs of infection, local swelling, heat, pain and redness, followed by effective intervention, is necessary to achieve prompt resolution. Infected wounds frequently have increased levels of exudate, pus and odour, and the patient might be pyrexial and/or have an elevated neutrophil count.

In clinical practice, a diagnosis of infection is based on the presence of the above symptoms, although many clinical indicators, such as inflammation and discharge, have a low predictive value of infection in wounds. Definitive diagnosis is achieved by microbiological analysis of wound samples. Tissue biopsy provides the most accurate results, but this is an invasive procedure that is difficult to achieve for the mass of specimens required. Wound swabbing is the most common wound sampling method used throughout the UK although its clinical value has been questioned. Furthermore, microbiological diagnosis of wound infection can take 48 to 72 hours, which allows time for infection to further develop if first-line/best-guess treatment is not employed immediately.

There therefore remains a need in the art for a method for the early diagnosis and prognosis of wound infection, and for devices and wound dressings for use in carrying out such methods.

Concentrations of reactive oxygen species (ROS) are known to rise in damaged tissues, producing a condition known as oxidative stress. ROS generation by inflammatory cells within the dermis play an important role in mediating wound healing. However, prolonged and more severe oxidative stress may delay healing because it will produce chronic inflammation, divert available energy supply towards antioxidant defence at the expense of tissue reconstruction, and increase levels of matrix metalloproteinases which cause tissue breakdown. A variety of cellular (enzymatic) and extracellular (non-enzymatic) antioxidant entities exist within normal and inflamed dermal tissues and fluids to counteract the direct effects of ROS by direct scavenging and by sequestering free transition metal ions.

It has been reported that the antioxidant activity of healing wounds is not significantly higher than that of non healing wounds. Recent evidence indicates that there is no significant difference in the total antioxidant capacity of acute and chronic wound fluid, although chronic wound fluid exhibited higher total antioxidant capacity when variations in wound fluid protein content were accounted for (Moseley et al., (2004) *Wound Repair and Regeneration* vol. 12, No. 4, 419-429).

DISCLOSURE OF THE INVENTION

The present inventors have found that the total antioxidant capacity of infected wound fluid is significantly higher (p=0.019) than that of fluid derived from non-infected wounds of similar type. It has further been found that total antioxidant capacity is the only marker of wound infection to correlate both with clinical signs of infection and with the total microbial burden of the wound.

Accordingly, in a first aspect, the present invention provides an indicator device adapted give a detectable signal when the antioxidant capacity of a sample exceeds a predetermined minimum level which is characteristic of an infection.

The term 'antioxidant capacity' refers to the ability of the wound fluid to inactivate reactive oxygen species such as hydroxyl radicals (.OH), singlet oxygen ($^1O_2$), hydroperoxyl radicals (.OOH), superoxide radical anions (.$O_2^-$) and hydrogen peroxide ($H_2O_2$). Preferably, the term "antioxidant capacity" refers to the rate at which the sample inactivates the above species, and in particular superoxide ($O_2^-$) anions.

Accordingly, the device according to the present invention preferably comprises a source of at least one reactive oxygen species, preferably a source of superoxide anions. For example, the device may comprise an oxidase enzyme and a substrate therefor, wherein reaction of the enzyme and the substrate results in the formation of a reactive oxygen species. Suitably, the enzyme is xanthine oxidase, and the substrate comprises hypoxanthine. Suitably, the device further comprises an indicator molecule that reacts with the reactive oxygen species to produce a detectable change. For example, the indicator molecule may be a redox indicator that is oxidized or reduced by the reactive oxygen species with consequential change in absorbance or fluorescence properties. Suitable redox indicators include: Cytochrome C, which exhibits a change in optical absorbance in the presence of superoxide; 1,10-phenanthrolene—iron salt which changes from pale blue to red when reduced; diphenylamine sulphonic acid which changes from red/violet to colourless when reduced, and triphenylmethane dyes. In addition, the starch-iodide reaction is suitable for use as an indicator of redox potential, reduction of the complex is indicated by a colour change from blue to colourless.

The antioxidants present in the sample compete with the redox indicator moiety in reacting with the reactive oxygen species, whereby the change in the rate of reaction of the indicator moiety can be used to obtain a quantitative measure of the total antioxidant capacity of the sample.

Preferably, the antioxidant capacity of a sample is determined by an assay based on the rate color change of Cytochrome C in the presence of a flux of superoxide. This method is described by van Gelder B F and Slater E C (1962) *Biochim Biophys Acta* 58: 593-595, and is also described in the article by Moseley et al. (op. Cit.). Briefly, the method comprises generating a flux of superoxide anions by reaction of hypoxanthine with xanthine oxidase. The superoxide reacts with a reference amount of Cytochrome C and with any other antioxidants present in the sample. The relative rate of change of the absorbance of the Cytochrome C gives a measure of the total activity of other antioxidants present.

Alternatively or additionally, the antioxidant activity may be measured by the diphenylpicrylhydrazyl (DPPH) test, for example as percentage reduction in absorbance at 524 nm after 4 hours of $10^{-4}$ M DPPH following addition of the sample, as described further in U.S. Pat. No. 5,667,501.

Alternatively or additionally, the antioxidant activity may be measured by its ability to inhibit the oxidation of ABTS (2,2'-azino-di-[3-ethylbenzthiazoline sulphonate]) by a peroxidase.

One or more of the reagents in the devices according to the invention may be conjugated to a solid substrate material in the device. The following paper gives a useful review of bioconjugation techniques for use in pharmaceutical chemistry: Veronese, F. M. and Morpurgo, M (1999) Bioconjugation in Pharmaceutical Chemistry II Farmaco, 54, 497-516 and Ulbrich, K., et al (2000) Journal of Controlled Release 64, 63-79. The entire contents of these papers are hereby incorporated by reference.

Suitable materials for forming the substrate include any suitable natural or synthetic polymer, including insoluble polysaccharides such as cellulose, and synthetic polymers such as polyacrylates, high density porous polyethylene sheet materials, polyvinyl chloride, polyvinyl acetate, copolymers of vinyl acetate and vinyl chloride, polyamide, polycarbonate, nylon, glass fiber, orlon, polyester, polystyrene, and mixtures and combinations thereof. Suitably, the substrate comprises pendant amine, ester or carboxylate groups to assist conjugation.

In a preferred embodiment, the sample comprises wound fluid. More preferably, the sample comprises chronic wound fluid.

The detectable signal produced by the device according to the present invention is observable or measurable by a physical, chemical, or biological means known to those of skill in the art. A detectable signal may be a change in emission or absorbance of electromagnetic waves at a certain wavelength, hybridization or enzymatic reaction. In preferred embodiments, detectable signals are changes in colour when viewed under white light, or fluorescence when viewed under UV light. In certain embodiments, the device may comprise an electronic sensor, for example to detect color change or fluorescence and to provide a quantitative output thereof. In yet other embodiments, the device may comprise an electrochemical sensor, for example a sensor of oxygen concentration similar to those commonly used to detect blood oxygen concentration, or a redox sensor to detect the redox potential of a sample relative to a standard potential. These sensors can provide a quantitative output in digital form.

The device preferably further comprises a reference assay element for determining the total protein content of the sample, so that the measured antioxidant level can be normalised to constant total protein level in order to increase accuracy.

The inventors have found that the antioxidant capacity of infected wound fluid is higher than that of non-infected wound fluid. The predetermined minimum antioxidant capacity of the sample may be at least about 130%, 135%, 140%, 145%, or 150% of the total antioxidant capacity of non-infected wound fluid from the same type of wound. Preferably, the indicator device enables the in vitro diagnosis of wound infection by the generation of a detectable signal when the antioxidant capacity of a sample exceeds the predetermined minimum level. Preferably, the indicator device is adapted to detect infection in chronic wound fluid.

In certain embodiments, the device according to the present invention comprises, or consists essentially of a wound dressing, dipstick or swab. In certain embodiments, the device according to the present invention comprises a housing containing one or more of the reagents and having an inlet provided therein for introduction of the sample. The housing may be at least partially transparent, or may have windows provided therein, for observation of the indicator moiety. In certain embodiments, the device operates on the lateral flow principle. That is to say, said device comprises a housing having an inlet for the sample and side walls defining a fluid lateral flow path extending from the inlet. By "lateral flow", it is meant liquid flow in which the dissolved or dispersed components of the sample are carried, preferably at substantially equal rates, and with relatively unimpaired flow, laterally through the carrier. Suitably, the fluid flow path contains one or more porous carrier materials. The porous carrier materials are preferably in fluid communication along substantially the whole fluid flow path so as to assist transfer of fluid along the path by capillary action. Suitably, the porous carrier materials are hydrophilic, but preferably they do not themselves absorb water. The porous carrier materials may function as solid substrates for attachment of reagents or indicator moieties. In certain embodiments of the present invention, the device further comprises a control moiety located in a control zone in said in said device, wherein the control moiety can interact with a component of the wound fluid sample to improve the accuracy of the device.

The devices according to the present invention may for example be incorporated into a bacterial sensing device of the kind described in copending application GB 0501818.9 filed on 28 Jan. 2005, the entire content of which is incorporated herein by reference.

Briefly, the devices of GB 0501818.9 are lateral flow sensors for the detection of endogenous and/or microbial protease enzymes in wound fluid in order to ascertain the amount and type of bacterial infection. The devices comprise: a housing having an inlet for the sample and side walls defining a fluid flow path extending from the inlet, an indicator moiety that is bound to a solid substrate by means of a peptide linker moiety that is cleavable by the analyte enzyme, the solid substrate being located in a reaction zone of the fluid flow path; and a detector moiety located in a detection zone downstream from the reaction zone in the fluid flow path, wherein the detector moiety can interact with an indicator moiety that has been cleaved from the solid substrate to produce a detectable change in the detection zone.

Endogenous (i.e. host-derived) protease enzymes that may be detected by the devices are suitably selected from the group consisting of matrix metalloproteinases (MMP's), elastase, stromelysin, kallikrein and thrombin. Suitably, the endogenous protease is selected from the group consisting of neutrophil proteases and macrophage proteases. Preferred protease enzymes include collagenases (e.g. MMP-1 and MMP-8), gelatinases (e.g. MMP-9) and neutrophil elastase, MMP-2, MMP-12, proteinase 3, plasmin, low molecular weight gelatinases and latent or active elastases, interleukin converting enzymes and tumor necrosis factor (TNFα) converting enzymes. Microbial enzymes that may be detected by the devices are suitably selected from the group consisting of protease enzymes that have been secreted by microorganisms, or expressed on the cell surface of microorganisms such as bacteria or fungi. Suitably, the microbial enzyme comprises a bacterial protease selected from the group consisting of bacterial enzymes of *Pseudomonas Aeruginosa, Escherichia Coli, Streptoccus Pyogenes* and *Staphylococcus Aureus*. The cleavable peptide linkers generally comprise cleavable oligopeptidic sequences, each typically of twenty residues or fewer, for example from 3 to 15 residues.

The above embodiments of the present invention share the special technical feature of a laterally spaced reaction zone and detection zone. This provides a compact, "lateral flow" analytical device that does not suffer from the disadvantages of prior art assays. In particular, since it uses a readily synthesised peptide linker in a substrate for the analyte enzyme, the reagents are inexpensive to prepare and stable under normal sterilization and storage conditions. Furthermore, the device detects active enzymes only, and does not give false positives for inactive enzymes or proenzymes.

The size and shape of the carrier are not critical and may vary. The carrier defines a lateral flow path. Suitably, the porous carrier is in the form of one or more elongate strips or columns. In certain embodiments, the porous carrier is one or more elongate strips of sheet material, or a plurality of sheets making up in combination an elongate strip. The reaction zone and detection zone would then normally be spaced apart along the long axis of the strip. However, in some embodiments the porous carrier could, for example be in other sheet forms, such as a disk. In these cases the reaction zone and detection zone would normally be arranged concentrically around the center of the sheet, with a sample application zone in the center of the sheet. In yet other embodiments, the carrier is formed of carrier beads, for example beads made from any of the materials described above. The beads may suitably be sized from about 1 micrometer to about 1 mm. The beads may be packed into the flow path inside the housing, or may be captured or supported on a suitable porous substrate such as a glass fiber pad.

It will be appreciated that the devices according to the present invention may be adapted to detect at least one analyte in addition to the total antioxidant capacity of the wound fluid. This can be done by the use of several different reagents in a single reaction zone, or preferably by the provision in a single device of a plurality of lateral flow paths each having different for detecting a different analyte. In certain embodiments, the plurality of lateral flow paths are defined as separate fluid flow paths in the housing, for example the plurality of lateral flow paths may be radially distributed around a sample receiving port. In some embodiments, the plurality of fluid flow paths are physically separated by the housing. In other embodiments multiple lateral flow paths (lanes) can be defined in a single lateral flow membrane by depositing lines of wax or similar hydrophobic material between the lanes.

An absorbent element is suitably included in the devices of the present invention. The absorbent element is a means for drawing the whole sample through the device by capillary attraction. Generally, the absorbent element will consist of a hydrophilic absorbent material such as a woven or nonwoven textile material, a filter paper or a glass fiber filter.

The device may further comprise at least one filtration element to remove impurities from the sample before the sample undergoes analysis. The filtration device may for example comprise a microporous filtration sheet for removal of cells and other particulate debris from the sample. The filtration device is typically provided upstream of the sample application zone of the fluid flow path, for example in the inlet of the housing or in the housing upstream of the inlet.

Preferably, the devices according to the present invention include a control moiety in a control zone of the device, wherein the control moiety can interact with a component of the wound fluid sample to improve the accuracy of the device. Suitably, the control zone is adapted to reduce false positive or false negative results. A false negative result could arise for various reasons, including (1) the sample is too dilute, or (2) the sample was too small to start with.

In order to address false negative mechanism, the control zone preferably further comprises a reference assay element for determining the total protease content or the total protein content of the sample, that is to say for establishing that the total protease content or the total protein content of the sample is higher than a predetermined minimum. It is possible to indicate the presence of protein by the use of tetrabromophenol blue, which changes from colorless to blue depending on the concentration of protein present. It is also possible to detect glucose (using glucose oxidase), blood (using diisopropyl-benzene dihydro peroxide and tetramethylbenzidine), leukocytes (using ester and diazonium salt). These may all be useful analytes for detection in the control zone for the reduction of false negatives.

In a further aspect, the present invention provides a diagnostic test system or kit comprising a diagnostic device according to the present invention. The test system or kit may comprise, in addition to a diagnostic device according to the present invention, one or more components selected from: a color chart for interpreting the output of the diagnostic device, a sampling device for collecting a sample of a wound fluid from a wound, a wash liquid for carrying a sample of wound fluid through the device, and a pretreatment solution containing a reagent for pretreatment of the wound fluid sample.

Where present, the sampling device may comprise a swab or a biopsy punch, for example a shaft having a swab or biopsy punch attached thereto. Suitably, the housing of the diagnostic device includes a sample receiving port in fluid communication with the inlet to the fluid flow path, and preferably the housing and the swab or biopsy punch comprise complementary fitting elements whereby the swab or biopsy punch can be secured to the housing with the swab or biopsy punch received in the sample receiving port.

In certain embodiments the fitting element on the shaft may be located from 1 mm to about 30 nm from the base of the swab or the biopsy punch. This is consistent with the use of relatively small sample receiving port on the housing of the diagnostic device. The sample receiving port is typically located on an upper surface of the diagnostic device, and it is typically generally in the form of an upwardly projecting tube, open at the top and having the inlet to the fluid flow path located at the bottom of the tube. Suitable swabs, biopsy punches and sample receiving caps are described in detail in copending applications GB0403976.4 and GB0403978.0 both filed on 23 Feb. 2004, the entire contents of which are incorporated herein by reference.

The fitting element on the shaft may a tapered region of the shaft for forming an interference fit with the housing, for example it may appear as a truncated cone that is coaxial with the shaft and tapers towards the first end of the shaft. Or the whole shaft may have a diameter larger than that of the swab or biopsy punch, with a tapered region adjacent to the first end. In any case, the diameter of the tapered region where it engages with the housing is normally greater than the diameter of the swab or biopsy punch, so that the inlet port can enclose the swab or biopsy punch.

In other embodiments, the engagement element may comprise a snap-fitting projection for forming a snap-fit with one or more complementary projections on an inner surface of the housing, or a threaded projection for forming a screw fit with one or more complementary threads on an inner surface of the cap, or a Luer-lock type fitting.

The swab may be any absorbent swab, for example a nonwoven fibrous swab. Typically the diameter of the swab is about 2 to about 5 mm, for example about 3 mm. In certain embodiments, the swab may be formed from a medically acceptable open-celled foam, for example a polyurethane foam, since such foams have high absorbency and can readily be squeezed to expel absorbed fluids. The biopsy punch will typically be a stainless steel cylindrical punch of diameter about 1 mm to about 10 mm, for example about 3 mm to about 8 mm, suitably about 6 mm.

In certain embodiments the shaft is hollow, whereby a fluid can be passed down the shaft from the second end to expel the biological sample from the swab or the biopsy punch into the diagnostic device. This helps to ensure that all of the sample passes through the porous carrier, thereby avoiding false negatives. The shaft may comprise a fitting at the second end for attachment of a syringe or other source of the fluid. In certain embodiments, the apparatus may comprise a reservoir of liquid attached to the second end of the shaft, for example a compressible bulb containing the liquid, which can be activated after use of the swab or biopsy punch. Suitable devices of this kind are described, for example in U.S. Pat. No. 5,266,266, the entire content of which is incorporated herein by reference. In other embodiments, the apparatus may comprise a plunger that can be pushed down the hollow bore of the shaft to expel fluid or other specimens from the swab or biopsy punch.

Another advantage of the hollow shaft is that, where the apparatus is a biopsy punch, the biopsy sample can more readily be pushed or blown out of the punch. The biopsy punch apparatus can further comprise a homogenizing tool that can be passed down the hollow shaft to homogenize a tissue sample in the biopsy punch. This step of homogenizing can be followed, if necessary, by passing liquid down the shaft from the second end to expel the homogenized tissue from the biopsy punch into the device for diagnostic analysis.

In this aspect of the invention, the swab or biopsy punch may be sterilized, and may be packaged in a microorganism-impermeable container. The diagnostic devices according to the present invention may also be sterilized, but they may not, because the devices often do not come into contact with the patient being diagnosed.

The invention also provides a system for use in the diagnosis and treatment of wounds comprising a diagnostic device according to the first aspect of the invention and a wound dressing comprising at least one antimicrobial agent. The wound dressing comprising the antimicrobial agent(s) can be applied to the wound selectively, when the diagnostic device indicates the presence of wound infection. This avoids unnecessary application of antimicrobial agents to the wound, which is desirable because most antimicrobial agents are cytotoxic and interfere with wound healing, and also to avoid the development of resistant microorganisms. Preferably, the system further comprises a wound dressing that is substantially free from antimicrobial agents, for application to the wound when the measured total antioxidant capacity is indicative of a non-infected wound. The system may be in the form of a kit, and the device and the wound dressing(s) may be packaged together in a single package.

In a further aspect, the invention provides a method for the early detection and/or quantification of wound infection, comprising determining the total antioxidant capacity in a sample of wound fluid. In certain embodiments, the method is adapted to determine whether the total antioxidant capacity in a sample of wound fluid exceeds a predetermined minimum level which is characteristic of an infection. In other embodiments, method is adapted to determine whether the total antioxidant capacity in a sample of wound fluid exhibits an increase over time that is indicative of the development of infection.

Preferably, the total antioxidant capacity of the sample is determined by one of the chemical or electrochemical assays described above in relation to the devices according to the first aspect of the invention.

Preferably, the method comprises the steps of contacting the indicator device of the first aspect of the invention with a sample, and assessing the generation of the detectable signal from the indicator device.

Preferably, the method is an in vitro method that is performed on a sample of wound fluid that has been removed from the body.

In a further aspect, the present invention provides a method for the treatment of a wound comprising the steps of measuring the total antioxidant capacity of a wound fluid collected from the wound, and applying an antimicrobial wound dressing to the wound selectively if the said total antioxidant capacity is indicative of wound infection.

The antimicrobial wound dressing used in this and other aspects of the invention comprises an effective amount of an antimicrobial agent, which may preferably be selected from the group consisting of antiseptics and antibiotics and mixtures thereof. Suitable antibiotics include peptide antimicrobials (e.g. defensins, Magainin, synthetic derivatives of them) tetracycline, penicillins, terramycins, erythromycin, bacitracin, neomycin, polymycin B, mupirocin clindamycin and mixtures thereof. Suitable antiseptics include silver sulfadiazine, chlorhexidine, povidone iodine, triclosan, other silver salts and colloidal silver, sucralfate, quaternary ammonium salts and mixtures thereof.

Preferably, the method further comprises applying a wound dressing that is substantially free of antimicrobial agents to the wound if the said total antioxidant capacity is indicative of absence of wound infection.

The wound dressing materials used in this aspect of the invention may for example be provided in the form of beads, flakes, powder, and preferably in the form of a film, a fibrous pad, a web, a woven or non-woven fabric, a freeze-dried sponge, a foam or combinations thereof. In certain embodiments, the dressing material is selected from the group consisting of woven fabrics, knitted fabrics, and nonwoven fabrics, all of which may be made by conventional methods. In other embodiments, the material may comprise (or consist essentially of) a freeze-dried sponge or a solvent-dried sponge.

The wound dressing material may be in the form of a solid, or a semi-solid ointment or gel. Preferably, the wound dressing material comprises only up to 20% by weight, preferably less than 10% by weight of water. The relatively low water content improves the stability of the material and makes it possible to sterilize by heat or irradiation without loss of activity. The material may also contain 0-40% by weight, preferably 0-25% by weight of a plasticiser, preferably a polyhydric alcohol such as glycerol. All of the above percentages are on a dry weight basis.

Preferably, the method comprises sampling the wound fluid at intervals, for example at intervals of from 1 hour to 24 hours, and selecting an antimicrobial or non-antimicrobial dressing to treat the wound at said intervals in response to the measured total antioxidant capacity. In certain embodiments, the wound dressing selection is determined by the absolute level of the measured antioxidant capacity, or it may be determined by the rate of change in the total antioxidant capacity, whereby an antimicrobial dressing is applied when an increase in total antioxidant capacity is detected, and a conventional non-antimicrobial dressing is applied if the total antioxidant level is constant or falling.

Preferably, the method further comprises determining the total protein content of the sample, whereby the measured antioxidant capacity can be normalised to constant total protein content.

Any type of wound may be diagnosed for treatment using the methods, devices and systems of the present invention. For example, the wound may be an acute wound such as an acute traumatic laceration, perhaps resulting from an intentional operative incision. More usually the wound may be a chronic wound. Preferably, the chronic wound is selected from the group consisting of venous ulcers, pressure sores, decubitis ulcers, diabetic ulcers and chronic ulcers of unknown aetiology. Chronic wound fluids may have antioxidant levels higher than the level found in normal, acute wound fluids. Nevertheless, it has been found that the levels of antioxidants increase still further in infected chronic wounds.

The term "wound fluid" herein refers to any wound exudate or other fluid (preferably substantially not including blood) that is present at the surface of the wound, or that is removed from the wound surface by aspiration, absorption or washing. The measuring is preferably carried out on wound fluid that has been removed from the body of the patient, but can also be performed on wound fluid in situ. The term "wound fluid" does not normally refer to blood or tissue plasma remote from the wound site.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±100%.

It will be appreciated that any feature or embodiment that is described herein in relation to any one aspect of the invention may also be applied to any other aspect of the invention. It will also be appreciated that any combination of the features described herein may also be used in the present invention.

All documents cited herein are incorporated by reference in their entirety.

MODES FOR CARRYING OUT THE INVENTION

Determination of Antioxidant Capacity by Cytochrome C Assay

Wound fluid samples from 10 infected and 10 non-infected Venous leg ulcer wound fluids were isolated. In a total volume of 1 ml of 100 mM potassium phosphate buffer, pH 7.8, a superoxide flux was generated by the oxidation of hypoxanthine (1 mM, Sigma) by xanthine oxidase (5 mU/ml; grade III Sigma). All reaction mixtures also contained cytochrome C (10 micro-M; horse heart type III Sigma). To determine the total antioxidant properties of the wound fluids, reaction mixtures were also established containing each of these samples (50 microlitres). Superoxide dismutase (40 U/mL, bovine erythrocytes, Sigma), an established scavenger of superoxide, was used as a positive control in this assay. Following initiation of the superoxide flux, the reduction of cytochrome C was monitored spectrophotometrically at room temperature and 550 nm, against a blank of all reagents minus the xanthine oxidase. Absorbance values were recorded at 20 second intervals for a total of 200 seconds, and all samples were measured in triplicate. The relative rates of superoxide production were calculated using the molar extinction coefficient of 21,000 mol/cm/l, followed by determination of the percentage inhibition of cytochrome C reduction by superoxide in the presence and absence of the wound fluid samples. Wound infection was determined by clinician and total microbial bioburden was determined. Results were as follows (standard deviations in brackets)

TABLE I

Percentage Inhibition of Cytochrome C Reduction by Superoxide

| Non-Infected Wound Fluids | Infected Wound Fluids |
| --- | --- |
| 28.89 (3.18) | 31.89 (6.47) |
| 21.99 (2.21) | 37.18 (0.67) |
| 20.95 (1.73) | 26.71 (3.03) |
| 15.77 (0.26) | 31.89 (4.07) |
| 27.63 (6.65) | 39.48 (4.03) |
| 20.73 (2.55) | 38.17 (1.34) |
| 29.35 (2.66) | 24.86 (0.54) |
| 21.75 (1.0) | 35.11 (4.52) |
| 40.63 (1.97) | 38.56 (1.96) |
| 33.37 (0.67) | 30.04 (0.55) |
| Mean % age = 26.1 | Mean % age = 33.4 |

The data in Table I show higher antioxidant capacity in the infected wound fluids than in the chronic wound fluids confirming that the infected wounds overproduce antioxidant factors.

The data measurements of total microbial bioburden showed a range of from about $2\times10^3$ to about $7\times10^8$ microorganisms. The measured total antioxidant capacity showed a substantially linear correlation when plotted against the logarithm of the total microbial bioburden.

Construction of a Diagnostic Device

Referring to FIGS. 1 to 4, the device comprises a housing 1, a swab 2 and a syringe 3. The housing 1 is generally disc-shaped with a tubular sample receiving port 6 projecting upwardly from the center of the disc in a generally cylindrical formation. The swab 2 comprises a collection sponge 8 of open-celled hydrophilic polyurethane foam, and a shaft of injection-molded thermoplastic. The shaft is provided at its lower end proximate to the sponge 8 with a radially enlarged region 10 that forms a substantially fluid-tight engagement inside the tubular receiving port 6 of the housing 1 by means of luer lock fittings on the enlarged region 10 and the inside surface 12 of the sample receiving port 6.

Figures 1, 7:
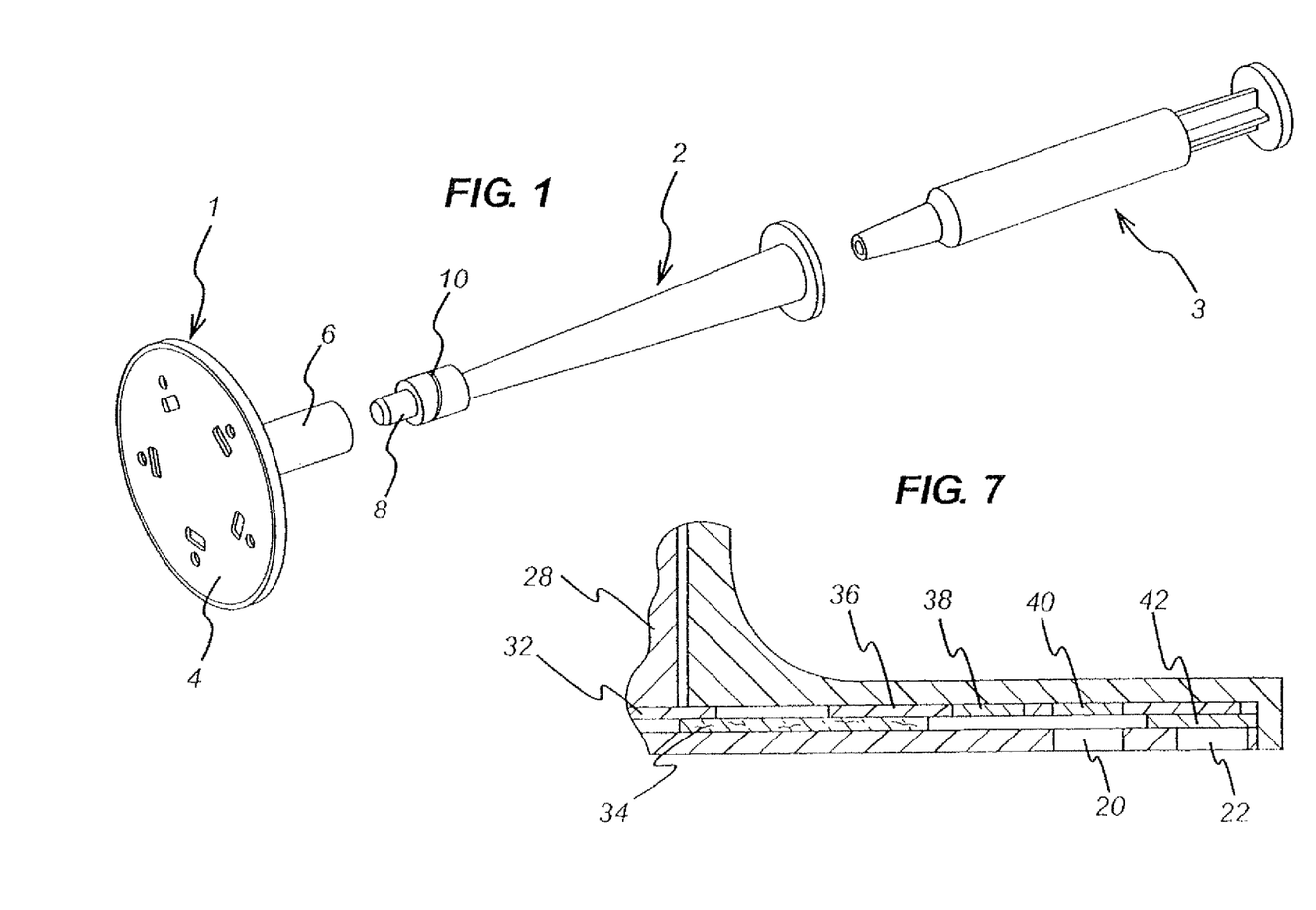
FIG. 1 is a perspective view of a diagnostic device according to the present invention.
FIG. 7 is a schematic partial cross-section through one of the fluid flow paths in a device according to the present invention, similar to that of FIG. 1, showing the different zones of the fluid flow path.
Figure 2:
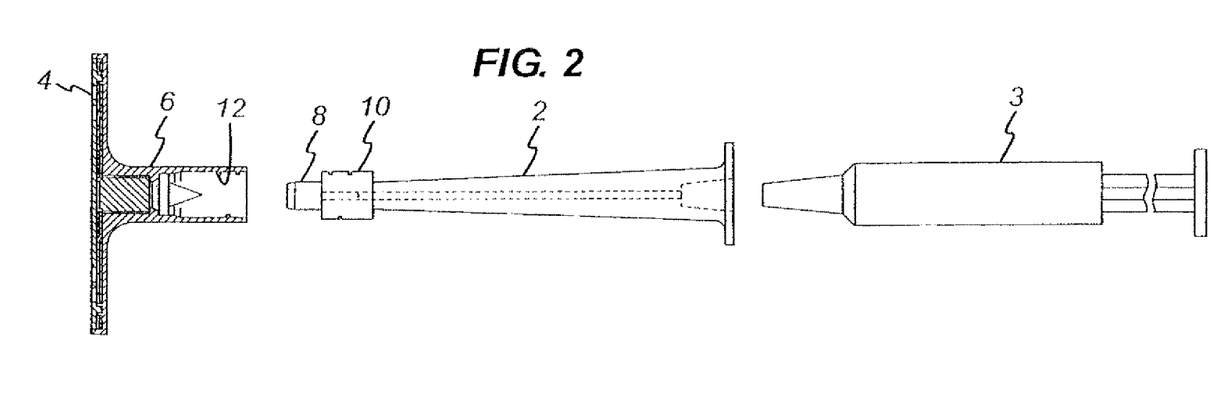
FIG. 2 is a longitudinal cross-section through the system of FIG. 1 before insertion of the swab into the sample receiving port of the device.
Figure 3:
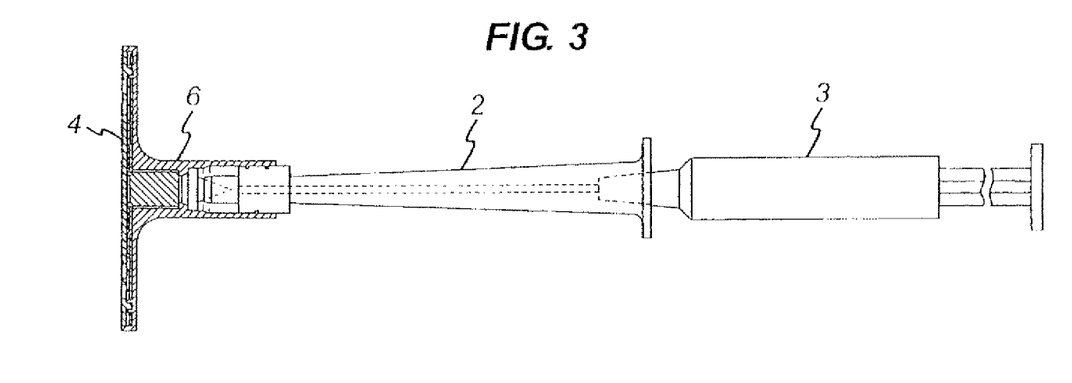
FIG. 3 is a longitudinal cross-section through the system of FIG. 1 after insertion of the swab into the sample receiving port of the device, and during the analysis using the device.

The shaft of the swab is hollow. The syringe 3 contains a predetermined volume of sterile saline solution for injection down the hollow shaft to expel the sample from the sponge 8 into the detection device, and to carry the sample through the fluid flow channel of the housing. In certain embodiments, the solution contains a reagent for the assay, or a binding partner or other inactivating agent for one or more interfering enzymes or other factors that may be present in the sample.

Figure 4:
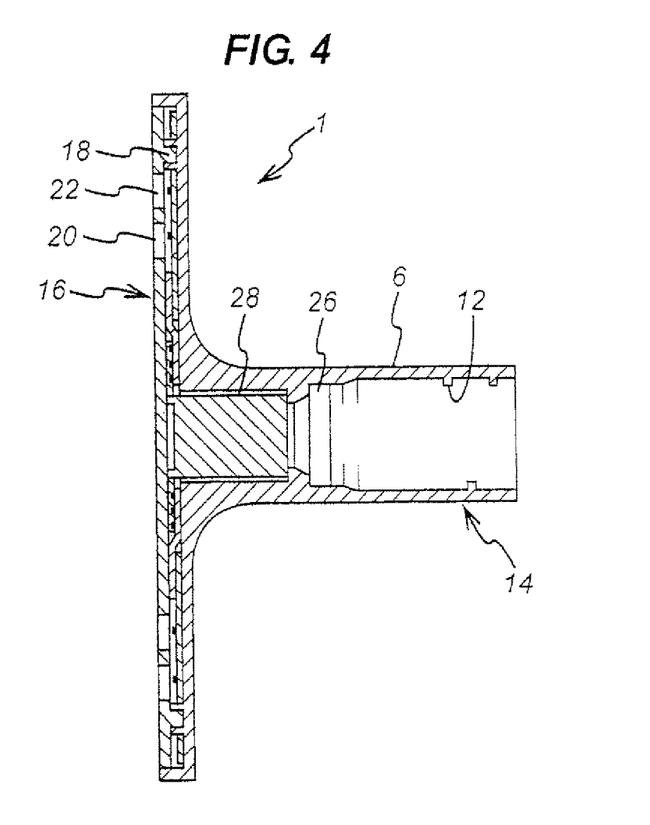
FIG. 4 is a more detailed longitudinal cross sectional view through the analysis device of FIG. 1.
Figure 5:
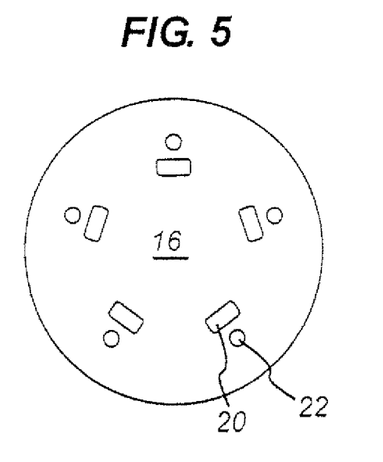
FIG. 5 is a bottom plan view of the analysis device of FIG. 1.
Figure 6:
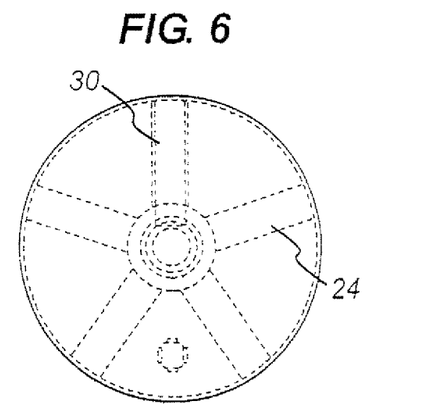
FIG. 6 is a bottom plan view of the analysis device of FIG. 1 with the bottom housing part removed.

Referring, to FIG. 4, the housing 1 is formed from an upper part 14 and a substantially disc-shaped lower part 16. Each part may be made by injection molding of thermoplastics. The upper housing part is itself made from two separate pieces. The parts are fitted together by means of snap fittings 18. The lower surface of the upper housing part 14 comprises five radially spaced shallow recesses 24 for receiving respective test strips 30 of porous carrier materials, as shown in FIG. 6. Each test strip may be adapted to test for a different analyte, or for a different concentration of the same analyte. The test strips are retained in the recesses by the lower housing part 16. The fluid flow paths for the samples extend between the upper and lower housing parts along the recesses 24 when the lower housing part 16 and the upper housing part 14 are snap-fitted together.

As already noted, a tubular sample receiving port 6 for receiving the swab projects upwardly from the upper housing part 14. A filter membrane can be located in the bottom of the inlet port in region 26 for removing particles and cells from the sample. The sample then flows through a cylindrical (annular) inlet channel 28 to the upstream ends of the five test strips 24.

The lower housing part 16 comprises apertures for viewing the test strips. For each of the radially disposed test strips there is a detection window 20 above the detection zone of the strip, and a control window 22 above the end-of-assay indicator region of the test strip. The lower surface of the second housing part may further be provided with embossing or other indicia identifying the specific protease or pathogen detected in that strip. It will be appreciated that the windows 20,22 and optional indicia could alternatively be provided in the upper housing part 14 if viewing from the top of the device is preferred.

Referring to FIG. 7, a schematic, enlarged cross-section perpendicular to one of the lateral flow paths of a device similar to that of FIG. 1 is shown. The flow path in this device contains a number of elements retained by the plastic housing. The first element in the flow path is a wicking pad 32 of non-woven textile material. This is located at the radially innermost end of the flow path, and positioned directly under the inlet channel 28 of the device. The wicking pad 32 is in capillary contact with reaction zone 34 of the flow path.

Reaction zone 34 is a porous glass fiber pad approximately 1 mm thick, 1 cm wide, and 3 cm long (i.e. extending about 3 cm radially outward from the inlet 28). The radially outermost end of the reaction zone pad 34 is in capillary contact with detection strip 36.

Finally, the radially outward end of the detection strip 36 is in capillary contact with absorbent reservoir 42, which acts to draw the liquid sample through the test strip and capture the liquid at the end of the strip. The absorbent reservoir 42 is a nonwoven rayon/polyacrylate strip of length about 3 cm that has been impregnated with a solution of 1% tetrabromophenol blue in distilled water and then dried. The indicator in the absorbent reservoir 42 changes color when it is soaked in the test solution, and this color change can be seen through window 22 of the housing. The color change can be used to confirm that a predetermined minimum volume of liquid sample has passed through the detection zone, thereby reducing the likelihood of false negative results. In an alternative embodiment, a device further comprises an electrochemical sensor 38.

In alternative embodiments, the swab may be replaced by a biopsy punch, optionally with means to macerate the sample.

In use, the swab is used to obtain a sample of wound fluid. Typically the sample will have volume about 100 ul of wound fluid. The swab is inserted into the sample receiving port of the device by means of the Luer lock. The sample is then expelled from the swab by injecting saline (sterile PBS) through the central channel of the swab from the syringe. The sample passes through the inlet channels and along the test strips. After a predetermined time, the underside of the device is viewed to assess the results of the analysis.

The above embodiments have been described by way of example only. Many other embodiments falling within the scope of the accompanying claims will be apparent to the skilled reader.

The invention claimed is:

1. A system for use in the diagnosis and treatment of wounds comprising a diagnostic device, the diagnostic device comprising an indicator device adapted to give a detectable signal when the antioxidant capacity of a sample of a mammalian wound fluid exceeds a predetermined minimum level which is characteristic of an infection, the indicator device comprising a housing containing one or more reagents, the housing having at least one inlet provided therein for introduction of the sample, wherein the indicator device comprises a source of at least one reactive oxygen species and an indicator molecule that reacts with the reactive oxygen species to produce a detectable change, and a wound dressing comprising at least one antimicrobial agent, the wound dressing to be applied to the wound when the measured total antioxidant capacity is indicative of an infected wound.

2. The system for use in the diagnosis and treatment of wounds of claim 1 comprising a diagnostic device, wherein the indicator device comprises a redox indicator molecule selected from the group consisting of Cytochrome C, 1,10-phenanthroline iron salt, diphenylamine sulfonic acid, triphenylmethane dyes, starch-iodine, diphenylpicryihydrazyl (DPPH) and 2,2'-azino-di(3-ethylbenzthiazoline sulfonate) (ABTS).

3. The system for use in the diagnosis and treatment of wounds of claim 1 comprising a diagnostic device, wherein the indicator device comprises an electrochemical sensor.

4. The system for use in the diagnosis and treatment of wounds of claim 1 comprising a diagnostic device, wherein the indicator device comprises a wound dressing, dipstick or swab.

5. The system for use in the diagnosis and treatment of wounds of claim 1 comprising a diagnostic device, which is a lateral flow diagnostic device.

6. The system for use in the diagnosis and treatment of wounds of claim 1 comprising a diagnostic device, wherein the indicator device is adapted to detect at least one further analyte in addition to the total antioxidant capacity of the sample.

7. The system for use in the diagnosis and treatment of wounds of claim 6 comprising a diagnostic device, wherein the at least one further analyte comprises total protein content of the sample.

8. A system for use in the diagnosis and treatment of wounds comprising a diagnostic device, the diagnostic device comprising an indicator device adapted to give a detectable signal when the antioxidant capacity of a sample of a mammalian wound fluid exceeds a predetermined minimum level which is characteristic of an infection, the indicator device comprising a housing containing one or more reagents, the housing having at least one inlet provided therein for introduction of the sample, wherein the indicator device comprises a source of at least one reactive oxygen species and an indicator molecule that reacts with the reactive oxygen species to produce a detectable change, and a wound dressing to be applied to the wound when the measured total antioxidant capacity is indicative of a non-infected wound.

9. The system for use in the diagnosis and treatment of wounds of claim 8 comprising a diagnostic device, wherein the device comprises a redox indicator molecule selected from the group consisting of Cytochrome C, 1,10-phenanthroline iron salt, diphenylamine sulfonic acid, triphenylmethane dyes, starch-iodine, diphenylpicryihydrazyl (DPPH) and 2,2'-azino-di(3-ethylbenzthiazoline sulfonate) (ABTS).

10. The system for use in the diagnosis and treatment of wounds of claim 8 comprising a diagnostic device, wherein the device comprises an electrochemical sensor.

11. The system for use in the diagnosis and treatment of wounds of claim 8 comprising a diagnostic device, wherein the device comprises a wound dressing, dipstick or swab.

12. The system for use in the diagnosis and treatment of wounds of claim 8 comprising a diagnostic device, which is a lateral flow diagnostic device.

13. The system for use in the diagnosis and treatment of wounds of claim 8 comprising a diagnostic device, wherein the device is adapted to detect at least one further analyte in addition to the total antioxidant capacity of the sample.

14. The system for use in the diagnosis and treatment of wounds of claim 13 comprising a diagnostic device, wherein the at least one further analyte comprises total protein content of the sample.

\* \* \* \* \*